United States Patent [19]
Champagne

[11] Patent Number: 5,626,476
[45] Date of Patent: May 6, 1997

[54] TECHNIQUE FOR REPAIRING TEETH

[76] Inventor: Richard Champagne, 88 Holly Dr., Eatontown, N.J. 07724

[21] Appl. No.: 671,332

[22] Filed: Jun. 27, 1996

Related U.S. Application Data

[63] Continuation-in-part of Ser. No. 637,834, Apr. 25, 1996.
[51] Int. Cl.⁶ .................................................. A61C 5/04
[52] U.S. Cl. ................................................ 433/226; 433/39
[58] Field of Search .......................... 433/39, 155, 156, 433/157, 214, 229

[56] References Cited

U.S. PATENT DOCUMENTS

| | | | |
|---|---|---|---|
| 388,620 | 8/1888 | Booth | 433/39 |
| 532,722 | 1/1895 | Dennis | 433/39 |
| 796,120 | 8/1905 | Green | 433/39 |
| 2,248,532 | 7/1941 | Hoffmann et al. | 433/39 |
| 3,082,531 | 3/1963 | Jacobson | 433/39 |
| 5,114,341 | 5/1992 | Kassel | 433/39 |

*Primary Examiner*—Nicholas D. Lucchesi
*Attorney, Agent, or Firm*—Jeffrey Kaplan, Esq.

[57] ABSTRACT

A double matrix band and technique for using the same is utilized in tooth repair to minimize interproximal spacing. The first portion of the matrix band is wrapped around the tooth adjacent to that being repaired, and the second portion of the band is then wrapped around the tooth to be repaired. Light permeable materials may be used for the matrix bands, thereby allowing tooth repair with light curable materials.

8 Claims, 6 Drawing Sheets

TECHNIQUE FOR REPAIRING TEETH

This application is a continuation-in-part of application Ser. No. 08/637,834, filed Apr. 25, 1996, now pending.

TECHNICAL FIELD

This invention is directed to dentistry, and more particularly to an improved technique of repairing large cavities in teeth.

BACKGROUND OF THE INVENTION

Those in the dentistry art have attempted for many years to devise improved techniques for repair of teeth, and specifically, for the restoration of large cavities and other damage to teeth. The most conventional materials include a silver mercury compound which is packed into the cavity and allowed to harden. Excess portions are then removed so that the tooth is substantially restored to its natural shape and form.

While the silver is somewhat unsightly, it is the mercury which is more of a concern. Mercury is a poisonous material and many individuals do not like the idea of having it used in their mouth. Accordingly, there has recently been a tendency to use other types of materials to repair teeth.

One set of such alternative materials are light curable resins. These materials have the physical property that they harden and bond to the teeth when exposed to a predetermined frequency of light. The frequency is typically that characteristic of ultraviolet. Typically, these materials are much more putty-like than the mercury silver materials which have substantially more body. These light curable materials are often applied using matrix bands to assist in the formation and shaping of the final restoration. The matrix bands provide a fixed volume to which the material is confined.

With reference to FIG. 1, shown therein is a top view of a damaged tooth 101 surrounded by two substantially undamaged teeth 102 and 103. It can be appreciated from FIG. 1 that the damage 104 in tooth 101 needs to be filled in with the silver mercury compound, the resin, or other material, in order to repair the tooth.

FIG. 2 shows the teeth of FIG. 1 with a matrix band 201 surrounding damaged tooth 101. In accordance with prior art techniques, the matrix band 201 is wrapped around tooth 101 and tightened by use of apparatus 202, commonly known as a matrix band and retainer. One commonly used type of such arrangement is known as a tofflemire retainer. The matrix band 201 is often constructed of thin metal, but may even be constructed of a thin light transparent film in case a light curable material, such as that previously discussed, is utilized to repair the damage 104.

The problem in the art is that the light permeable material is similar to a film, and is extremely thin and flimsy, much more so than the metal. The light permeable film wraps quite tightly around the damaged tooth, and thus leaves a large gap between, for example, teeth 101 and 103. This gap 207 is clearly shown in FIG. 2.

Ideally, it would be desirable for the restored tooth to be anatomically similar to the original tooth. This means that adjacent teeth should contact each other in the upper one-third portion of the interproximal area, and not contact one another along the remainder thereof. This is shown in FIG. 11.

FIG. 3 shows a similar arrangement to that of FIG. 2 except that the matrix band 301 is now constructed of a thin metallic material. Since the metal is much thicker and less malleable, the matrix band does not fully conform to the shape of tooth 101, but rather, is somewhat separated from tooth 101, at the sides thereof. As a result, the matrix band abuts, or nearly abuts, adjacent teeth 102 and 103 as shown. Indeed, the difference between FIGS. 2 and 3 can best be appreciated by viewing the interproximal spacing in both figures between teeth 102 and 101, and between teeth 103 and 101. It can be appreciated from FIG. 2 that filling in the bonding material to damaged portion 104 in FIG. 2 will result in large interproximal spacing between teeth 101 and 103. On the other hand, filling the bonding material into damaged portion 104 in FIG. 3 will result in much less interproximal spacing. However, since the matrix band of FIG. 3 is metallic, no light curable material can be used. The matrix band will not allow the light to permeate through to the curable material.

Those of ordinary skill in this art appreciate the desirability of minimizing interproximal spacing along the top portions of the teeth. For example, large interproximal spacing results in food debris being trapped between the teeth after repair. Other problems include periodontal disease, potential tooth decay, and orthodontic shifting, even resulting in a potential change of the patient's bite.

However, in view of the above discussion, it can also be appreciated that it is difficult to minimize interproximal spacing, in any part of the interproximal area, if a light curable material is used for tooth repair. This problem is due to the fact that the thin flimsy film-like material which is used to construct matrix bands for use in connection with light curable material conforms to the tooth being repaired, as shown in FIG. 2.

In view of the above, it can be appreciated that there exists a need in the art for a better technique of allowing light curable materials to be utilized in the repair of damaged teeth to obtain anatomically correct restorations.

SUMMARY OF THE INVENTION

The above and other problems of the prior art are overcome in accordance with the present invention which relates to a technique of permitting light curable bondable materials to be utilized in the repair of teeth, while simultaneously permitting an anatomically correct restoration which results in minimal interproximal spacing along a portion thereof and slightly larger interproximal spacing along the remaining length thereof. In accordance with the inventive technique, two light permeable matrix bands are utilized, the bands being joined at a predetermined small portion along the length thereof. The joined portion is placed in the interproximal area and one of the two matrix bands is anchored to a tooth adjacent to the tooth to be repaired. The second matrix band is then anchored around the tooth to be repaired. The resulting set of matrix bands leaves minimal interproximal spacing, at least near the top of the teeth, after the tooth is repaired yet allows use of light permeable materials in the construction of these bands.

Enhancements to the technique include the use of spacers impregnated with an astringent, and a novel double tofflemire retainer for tightening both matrix bands. The spacers provide slight separation near the gum line, yet do not affect the minimal interproximal spacing near the top of the teeth, thus resulting in an anatomically correct restoration. The double tofflemire retainer provides for ease of use. Each of the enhancements can be used to facilitate use of the improved technique.

DETAILED DESCRIPTION OF THE PREFERRED EMBODIMENT

Figures 4, 5:
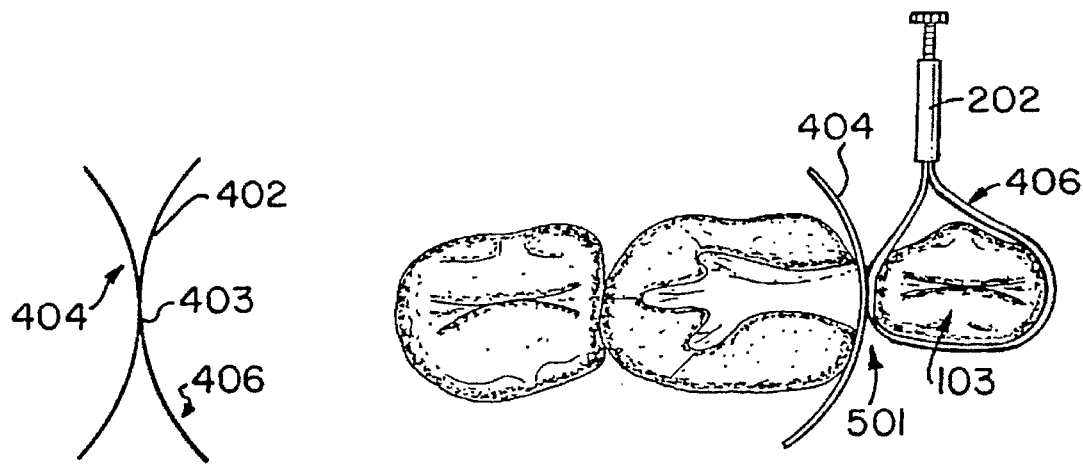
FIG. 4 shows an exemplary embodiment of applicant's novel technique for repairing the damaged tooth structure shown in FIG. 1.
FIG. 5 is an example of a double matrix band in accordance with the present invention, shown partially installed.
Figure 11:
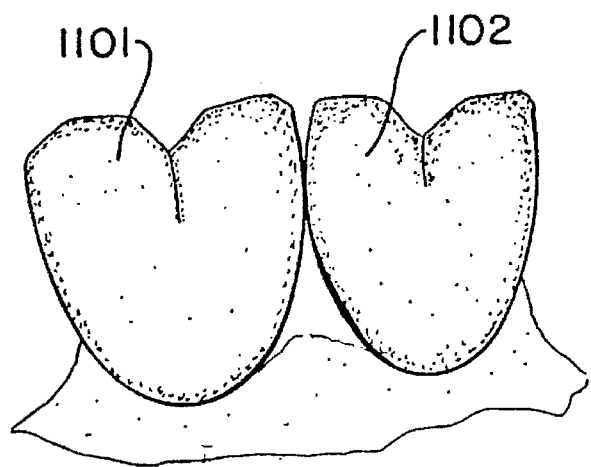
FIG. 11 shows anatomically correct interproximal spacing.

FIG. 4 shows a side view of applicants double matrix band 402 connected along an exemplary length 403. The connection along length 403 may be accomplished utilizing any acceptable glue, or alternatively, the entire double matrix band 402 may be molded from the same material, thereby resulting in section 403 simply being one single piece. As described more fully later herein and with respect to FIG. 11, connection point 403 should preferably not run the entire width of the matrix bands 404 and 406.

The length of sides 404 and 406 may be the same or different from each other, and a typical such length might be approximately two inches. The connection point 403 should be approximately one-quarter length from the end of each single matrix band 404 and 406. This leaves one half inch on one side of the connection, and one and one half inches on the other side thereof.

FIG. 5 shows the teeth 101 through 103, with the interproximal spacing 501 slightly exaggerated for explanation purposes. In operation, single band 406 is wrapped about undamaged tooth 103 as shown. The single band 406 is tightened using, for example, a tofflemire retainer 202. It is noted that the wrapping and tightening of matrix band 406 may be accomplished utilizing means other than a tofflemire retainer, such as that described in U.S. Pat. No. 4,553,937 to Ropers. In any event, as shown in FIG. 5, the wrapping and tightening of band 406 about tooth 103 is accomplished prior to the wrapping and tightening of matrix band 404 about damaged tooth 101.

Figure 1:
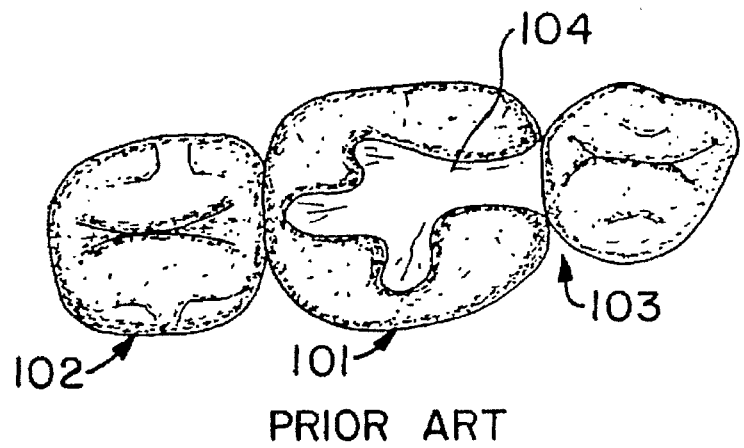
FIG. 1 shows three consecutive teeth, where a center one thereof has been damaged.
Figure 2:
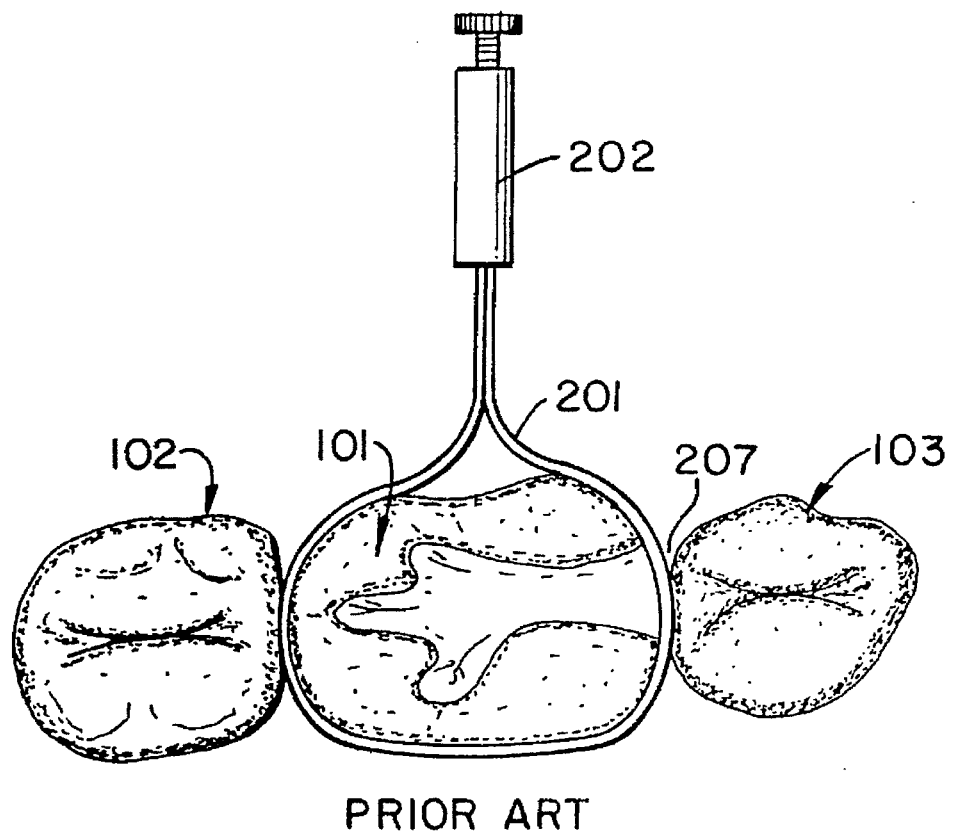
FIG. 2 shows prior art use of a technique for repairing such teeth.
Figure 3:
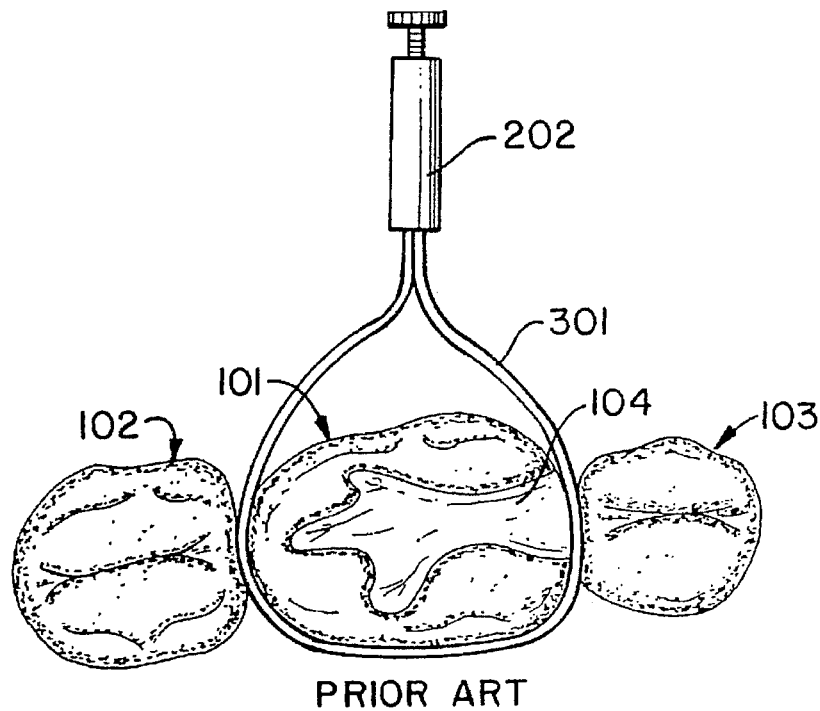
FIG. 3 shows an additional prior art technique for repairing of teeth.
Figure 6:
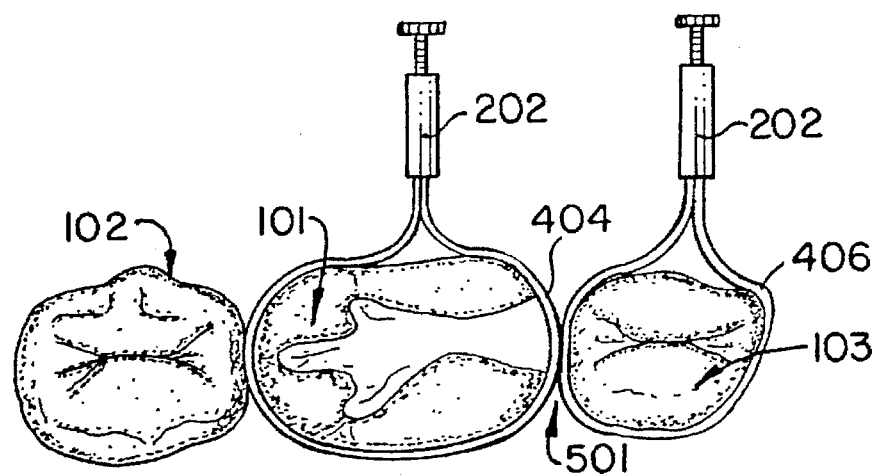
FIG. 6 is a more fully installed double matrix band in accordance with the present invention.

FIG. 6 shows the same three teeth 101 through 103, where the interproximal spacing 501 between teeth 101 and 103 has again been exaggerated. An additional tofflemire retainer 202 is connected to matrix band 404 for tightening thereof. It will be noted however, that as matrix band 404 is tightened about damaged tooth 101, the interproximal spacing 501 remains within the matrix band which will be filled with the repaired material. Accordingly, when one compares FIGS. 2 and 6, it is noted that the light curable material in FIG. 6 will extend out to tooth 103, thereby minimizing interproximal spacing. In FIG. 2, the light curing material will not extend to tooth 103, and a large interproximal spacing between teeth 101 and 103 will result after tooth repair. Thus, FIG. 6 provides a technique for allowing the matrix bands to be made of flimsy light permeable material, while still minimizing interproximal spacing.

In essence, matrix band 406 is utilized as an anchor to pull matrix band 404 away from the surface of the tooth 101, thus including the interproximal spacing 501 in the volume defined by matrix band 404. Such pulling action keeps the matrix band from tightly conforming to the tooth to be repaired.

The described technique utilizes a tooth next to the tooth being repaired in order to hold the matrix band 404 away from the area to be repaired. Of course, it is possible to utilize still a third matrix band and retainer about tooth 102 in order to minimize the interproximal spacing between teeth 101 and 102. Additionally, the double matrix band 402 may be intentionally fabricated thinner along the lengths 403 then along the remainder of the length, thereby further minimizing interproximal spacing.

Figure 7:
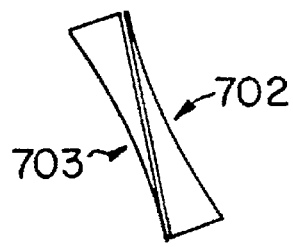
FIG. 7 is a set of wedges, preferably impregnated with an astringent.
Figure 8:
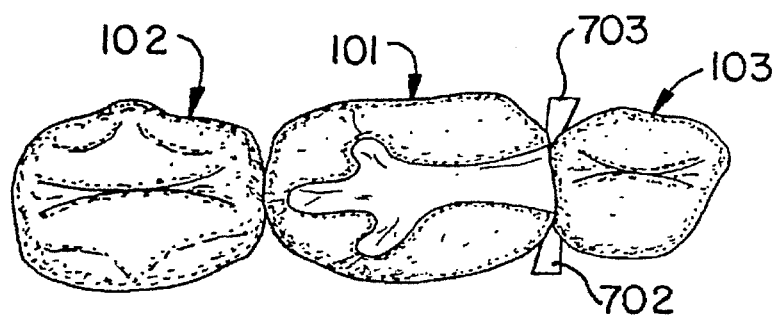
FIG. 8 shows the spacers of FIG. 7 as installed between teeth.

FIG. 7 shows two wedged shaped members 702 and 703 which may be utilized in conjunction with the invention in order to further minimize the interproximal spacing which results after tooth repair. As shown in FIG. 8, the two wedge members 702 and 703 are wedged between teeth 101 and 103 to thereby further open up a gap between these teeth before the previous inventive technique is applied. The wedges in FIG. 7, when placed between the teeth near the gum line, assist in making the interproximal space near the gum line slightly larger than near the top of the teeth. The use of two wedges results in a more anatomically correct structure as can be seen from FIG. 8. Thereafter, when the wedges are removed, the teeth spring back, further minimizing interproximal spacing.

Figure 9:
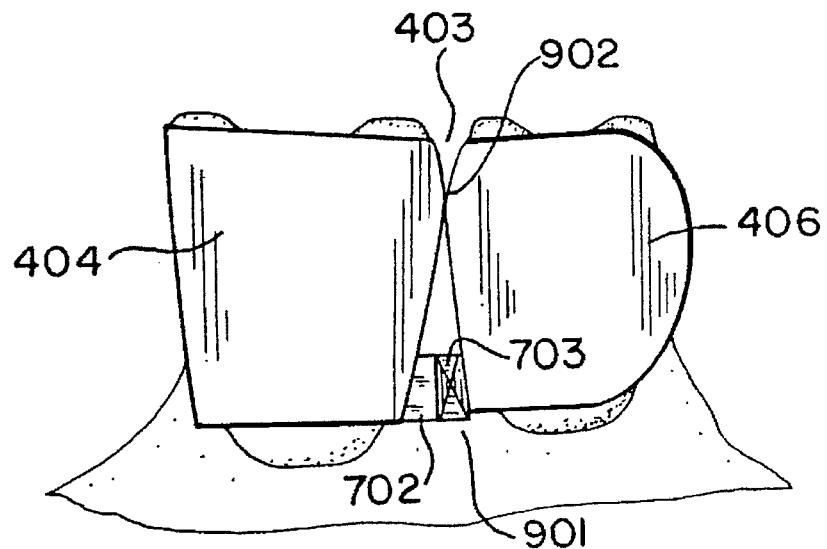
FIG. 9 is a side view of two teeth wrapped by the inventive double matrix band and separated by two wedges.

FIG. 9 shows how the wedges may be utilized between the double matrix band 402 and the patient's gum line 901. The double matrix band 402 is not connected along its entire width, but rather, only along a small portion 902 thereof. The wedging members 702 and 703 are wedged between the matrix bands 404 and 406, near the gum line 901. To accommodate these wedging members, the matrix band 404 and 406 are not connected below portion 902.

An additional enhancement is achieved by noting that the properties of many light curable materials are such that curing is inhibited if the material comes into contact with blood. It is therefore optimally desirable to impregnate the wooden wedging members 702 and 703 with a suitable astringent, so that in the event that the gum is irritated and bleeds, clotting will occur quickly.

Figure 10:
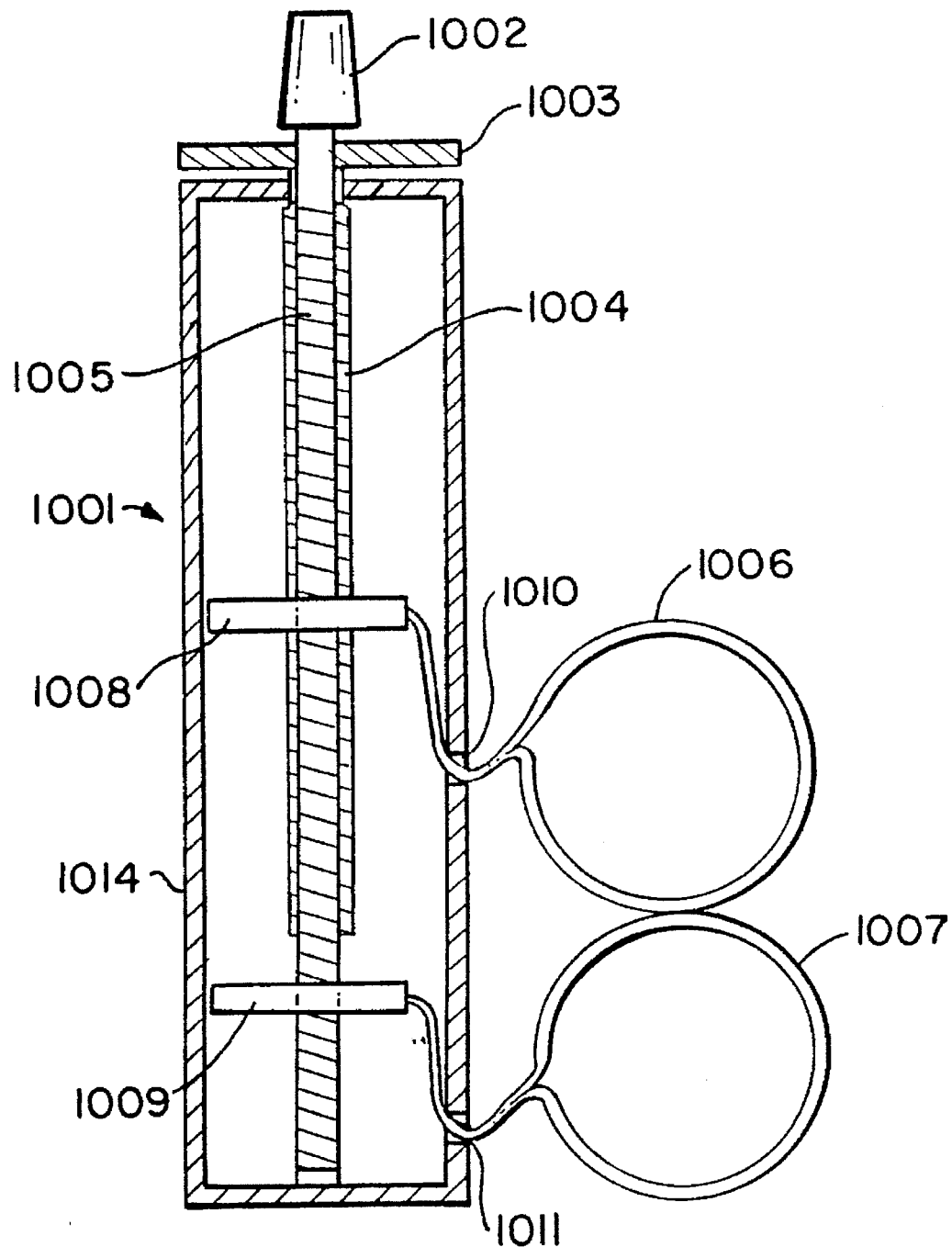
FIG. 10 shows a novel tightening apparatus for use with the inventive technique.

FIG. 10 shows a tightening apparatus for use with the inventive technique. The apparatus of FIG. 10 is quite similar to that commonly termed a tofflemire retainer, with the exception there are two independent matrix bands 1006 and 1007, and two independent tightening knobs 1002 and 1003.

For explanation purposes herein, we term the apparatus of FIG. 10 a double tofflemire retainer. The double tofflemire retainer 1001 comprises a body 1014, and first and second tightening knobs 1002 and 1003 respectively. The tightening knob 1002 is connected to a threaded shaft 1005, while the lower tightening knob 1003 is connected to an outer shaft 1004. The tightening knobs and shafts are arranged, as shown in FIG. 10, such that they can be turned independently of one another.

The threads on each shaft 1004 and 1005 engage a separate one of grasping members 1008 and 1009. Each of the grasping members 1008 and 1009 is connected, as shown, to a separate one of matrix bands 1006 and 1007. The matrix bands are threaded through openings 1010 and 1011, also as clearly indicated in the figure.

In operation, one of matrix bands 1006 to 1007 is wrapped about a tooth adjacent to a tooth to be repaired, and the other of the matrix bands 1006 and 1007 is wrapped about the tooth to be repaired. The tightening knob 1002 or 1003 which is connected to the appropriate matrix band corresponding to the tooth adjacent to that being repaired is first tightened and the other knob is then tightened so that the arrangement of FIG. 6 results.

Figure 12:
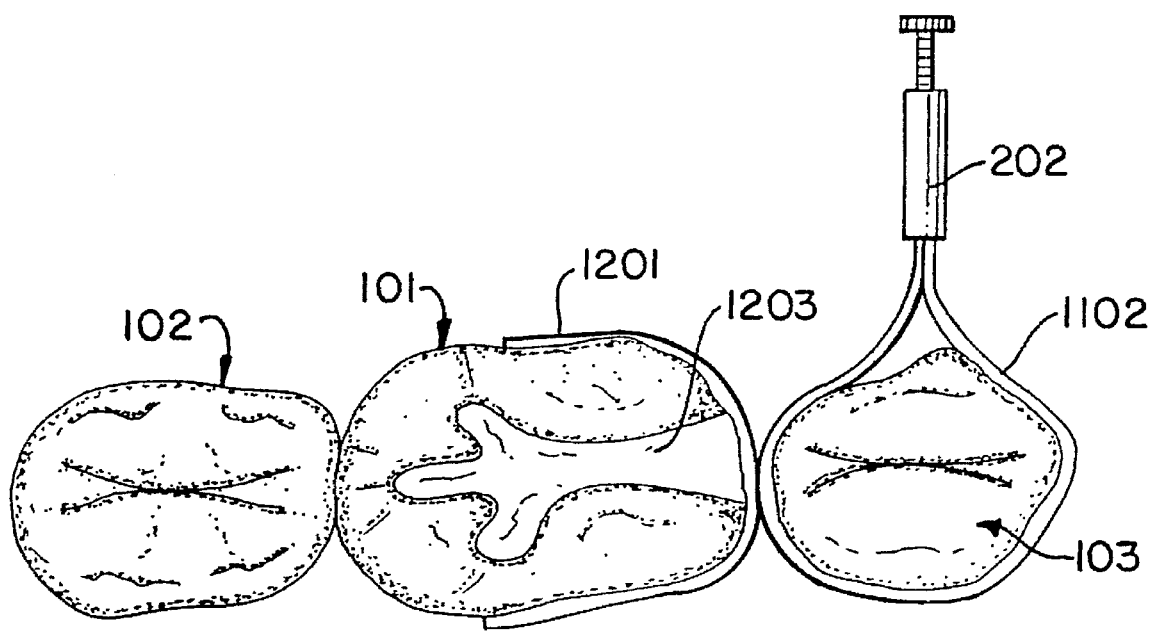
FIG. 12 shows an alternative embodiment of the invention.

FIG. 12 shows an alternative embodiment of the invention wherein the partial matrix band is utilized for tooth repair. Matrix band 1201 is a partial band which may be constructed of metal and which is permanently molded into a C-shape as shown. The tightening of matrix band 1202 by tofflemire retainer 202 causes matrix band 1101 to remain adjacent to tooth 103 while surrounding tooth 101 as shown. The repair material can then be placed in volume 1203, which, as can be seen from FIG. 12, comprises substantially all interproximal spacing between teeth 101 and 103.

While the above describes the preferred embodiment of the invention, it will be apparent to those of ordinary skill in the art that various other modifications and/or additions may be constructed without violating the spirit or scope of this invention. The above and other embodiments are intended to be covered by the following claims.

What is claimed is:

1. A method of repairing a tooth to be repaired comprising the steps of:

wrapping a matrix band around a tooth adjacent to said tooth to be repaired, said matrix band having a partial matrix band attached thereto; and placing said partial matrix band partially around said tooth to be repaired, thereby forming a volume between said partial matrix band and said tooth to be repaired said volume including substantially all interproximal spacing between said tooth to be repaired and said adjacent tooth; and filling said volume with repair material.

2. The method of 1 wherein said matrix band and said partial matrix band are constructed of metallic material.

3. Apparatus for restoration of a decayed tooth to be repaired, comprising:

anchor means for attaching to a tooth adjacent to said tooth to be repaired;

band means connected to said anchor means and adapted to be held in an interproximal spacing between said decayed tooth and said adjacent tooth with said band means extending only partially around said tooth to be repaired; and means for attaching said anchor means to said adjacent tooth such that said band means defines a volume comprising substantially all of said interproximal spacing.

4. Apparatus of claim 3 wherein said band means is constructed of a metallic material.

5. Apparatus of claim 3 where said band means is constructed of non-metallic material.

6. Apparatus of claim 3 wherein said anchor means is constructed of metallic material.

7. Apparatus of claim 3 wherein said anchor means is constructed of non-metallic material.

8. Apparatus of claim 3 wherein said anchor means and said band means are constructed of different materials.

* * * * *